United States Patent [19]

Perronnet et al.

[11] 4,128,562
[45] Dec. 5, 1978

[54] NOVEL 3-(PHOSPHORYLOXY) AND (PHOSPHONYLOXY)-THIOPHENES

[75] Inventors: Jacques Perronnet, Paris; Laurent Taliani, Les Pavillons-sous-Bois, both of France

[73] Assignee: Roussel Uclaf, Paris, France

[21] Appl. No.: 850,922

[22] Filed: Nov. 14, 1977

Related U.S. Application Data

[63] Continuation of Ser. No. 652,718, Jan. 27, 1976, abandoned.

[30] Foreign Application Priority Data

Feb. 14, 1975 [FR] France .................. 75 04628

[51] Int. Cl.$^2$ .............. C07D 333/16; C07D 333/00; A01N 9/36
[52] U.S. Cl. .............. 260/332.3 R; 260/329 P; 260/329 S; 424/202
[58] Field of Search .............. 260/332.3 R, 329 P, 260/329 S, 940

[56] References Cited

U.S. PATENT DOCUMENTS

| | | | |
|---|---|---|---|
| 3,131,120 | 4/1964 | Chupp et al. | 260/940 |
| 3,164,623 | 1/1965 | Schrader | 260/940 |
| 3,671,547 | 6/1972 | Stevick | 260/329 |

Primary Examiner—A. Siegel
Attorney, Agent, or Firm—Hammond & Littell

[57] ABSTRACT

Novel 3-(phosphoryloxy) or (phosphonyloxy)-thiophenes of the formula

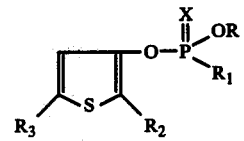

wherein R is alkyl of 1 to 4 carbon atoms, $R_1$ is selected from the group consisting of alkyl of 1 to 4 carbon atoms, alkoxy of 1 to 4 carbon atoms and

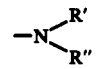

wherein R' and R" are individually selected from the group consisting of hydrogen and alkyl of 1 to 4 carbon atoms, $R_2$ is selected from the group consisting of cyano, alkoxy carbonyl of 2 to 4 carbon atoms and

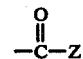

wherein Z is selected from the group consisting of phenyl and alkyl of 1 to 4 carbon atoms, $R_3$ is selected from the group consisting of alkyl of 1 to 6 carbon atoms, alkoxy of 1 to 6 carbon atoms, alkylthio of 1 to 6 carbon atoms, phenyl, morpholino, piperidinyl and alkoxy carbonyl of 2 to 4 carbon atoms and X is selected from the group consisting of oxygen and sulfur having pesticidal properties and their preparation.

8 Claims, No Drawings

NOVEL 3-(PHOSPHORYLOXY) AND (PHOSPHONYLOXY)-THIOPHENES

This is a continuation, of Ser. No. 652,718, filed Jan. 27, 1976 now abandoned.

STATE OF THE ART

Commonly assigned U.S. application Ser. No. 357,820 filed May 7, 1973 describes 3-phosphoryloxy-isothiazoles as having insecticidal and acaricidal properties.

OBJECTS OF THE INVENTION

It is an object of the invention to provide the novel 3-phosphoryloxy and (phosphonyloxy)-thiophenes of formula I and to provide a process for their preparation.

It is another object of the invention to provide novel pesticidal compositions and to provide a novel process for killing pests, particularly insects, nematodes and acariens.

These and other objects and advantages of the invention will become obvious from the following detailed description.

THE INVENTION

The novel 3-(phosphoryloxy) and (phosphonyloxy)-thiophenes of the invention have the formula

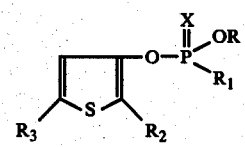

wherein R is alkyl of 1 to 4 carbon atoms, $R_1$ is selected from the group consisting of alkyl of 1 to 4 carbon atoms, alkoxy of 1 to 4 carbon atoms and

wherein R' and R'' are individually selected from the group consisting of hydrogen and alkyl of 1 to 4 carbon atoms, $R_2$ is selected from the group consisting of cyano, alkoxy carbonyl of 2 to 4 carbon atoms and

wherein Z is selected from the group consisting of phenyl and alkyl of 1 to 4 carbon atoms, $R_3$ is selected from the group consisting of alkyl of 1 to 6 carbon atoms, alkoxy of 1 to 6 carbon atoms, alkylthio of 1 to 6 carbon atoms, phenyl, morpholino, piperidinyl and alkoxy carbonyl of 2 to 4 carbon atoms and X is selected from the group consisting of oxygen and sulfur.

Suitable examples of R and $R_1$ are methyl, ethyl and straight or branched chain propyl or butyl while $R_1$ may further be methoxy, ethoxy, branched or straight chain propoxy or butoxy, amino, methylamino, ethylamino, propylamino, isopropylamino, butylamino, dimethylamino, diethylamino, dipropylamino or dibutylamino. Suitable examples of $R_2$ are cyano, methoxycarbonyl, ethoxycarbonyl, propoxycarbonyl, butoxycarbonyl, acetyl, propionyl, butyryl or benzoyl and suitable examples of $R_3$ are methyl, ethyl, straight or branched-chain propyl or butyl or pentyl, hexyl, methoxy, ethoxy, propoxy, butoxy, methylthio, ethylthio, propylthio, butylthio, phenyl, morpholino, piperidinyl, methoxycarbonyl, ethoxycarbonyl, propoxycarbonyl or butoxycarbonyl. X is either oxygen or sulfur.

Among the preferred compounds of formula I, R is alkyl of 1 to 4 carbon atoms, $R_1$ is alkoxy of 1 to 4 carbon atoms, $R_2$ is cyano, $R_3$ is alkyl of 1 to 6 carbon atoms or alkoxy of 1 to 6 carbon atoms and X is oxygen.

The novel process of the invention for the preparation of thiophenes of formula I comprises reacting a thiophene of the formula

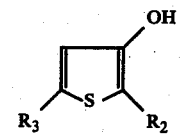

wherein $R_2$ and $R_3$ have the above definitions with a phosphorus reactant of the formula

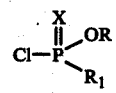

wherein X, R and $R_1$ have the above definitions. The reaction is preferably effected in an organic solvent such as acetone, acetonitrile, dimethylformamide or tetrahydrofuran and in the presence of a basic agent such as potassium carbonate, sodium hydride or triethylamine.

The starting materials of formula II are described in the literature or can be made by known procedures. For example, 2-cyano-3-hydroxy-5-methyl-thiophene and 2-cyano-3-hydroxy-5-phenyl-thiophene are described by Hedegaard et al/Tet., Vol. 27 (1971), p. 3853 and p. 3858/, 2,5-dicarbomethoxy-3-hydroxy-thiophene is described by Fiesselmann et al/Ber., Vol. 89 (1936), p. 1897/, 2-methoxycarbonyl-3-hydroxy-5-methyl-thiophene is described by Jacobsen et al/Tet., Vol. 21 (1965), p. 3331/ and 2-benzoyl-3-hydroxy-5-methoxy-thiophene and 2-methoxy-carbonyl-3-hydroxy-5-methoxy-thiophene have been described by Raap/Can. J. Chem., Vol. 46 (1968), p. 2255-58/, 2-cyano-3-hydroxy-5-methoxy-thiophene, 2-cyano-3-hydroxy-5-(N-morpholino)-thiophene, 2-cyano-3-hydroxy-5-ethylthio-thiophene, 2-cyano-3-hydroxy-5-n-butoxy-thiophene and 2-cyano-3-hydroxy-5-n-propyl-thiophene can be made by known procedures such as illustrated in the examples.

The novel pesticidal compositions of the invention are comprised of an effective amount of at least one compound of formula I and an inert carrier. The compositions may be in the form of powders, granules, suspensions, emulsions or solutions containing the active ingredient admixed, for example, with a vehicle and/or a cationic, anionic, or nonionic surface active agent to ensure a uniform dispersion of the substances in the compositions. The vehicle may be a liquid such as water, alcohols, hydrocarbon or other organic solvents, a mineral, animal or vegetable oil or a powder such as talc, clays, silicates or kieselguhr.

The liquid or powder compositions for foliar spraying preferably contain 10 to 80% by weight of the active material when used for insecticidal purposes and 20 to 80% by weight of the active material when used for acaricidal purposes. The liquids or powders used to treat soil for nematocidal purposes preferably contain 20 to 80% by weight of active material.

The novel method of the invention for combatting pests comprises contacting the pests with a lethal amount of at least one compound of formula I.

In the following examples there are described several preferred embodiments to illustrate the invention. However, it should be understood that the invention is not intended to be limited to the specific embodiments.

EXAMPLE 1

2-cyano-3-(dimethoxyphosphoryloxy)-5-methyl-thiophene 14 g of potassium carbonate and 8.9 ml of 0,0-dimethyl chlorophosphate were added to a solution of 14 g of 2-cyano-3-hydroxy-5-methyl-thiophene in 300 ml of acetone and the mixture was stirred for 15 hours at 20° C. and was evaporated to dryness. The residue was added to water and the aqueous phase was extracted with ether. The ether extracts were washed with 0.1N sodium hydroxide, dried, treated with activated carbon and was filtered. The filtrate was evaporated to dryness to obtain 12 g of product which was chromatographed over silica gel. The product was eluted with an 8-2 cyclohexane-ethyl acetate mixture and was washed with 0.1N sodium hydroxide to obtain a microanalytical sample of 2-cyano-3-(dimethoxyphosphoryloxy)-5-methyl-thiophene with a refractive index $n_D^{20} = 1.5165$.

Analysis: $C_8H_{10}NO_4PS$. Calculated: %C, 38.86; %H, 4.08; %N, 5.67; %P 12.53. Found: %C, 39.5; %H 4.2; %N, 5.7; %P, 12.2.

EXAMPLE 2

2-cyano-3-(dimethoxythiophosphoryloxy)-5-methyl-thiophene 11.2 g of potassium carbonate and 12.8 g of 0,0-dimethyl chlorothiophosphate were added to a solution of 11.2 g of 2-cyano-3-hydroxy-5-methyl-thiophene in 200 ml of acetone and the mixture was stirred for 15 hours at 20° C. and was then filtered. The filtrate was evaporated to dryness and the residue was chromatographed over silica gel. Elution with a 7-3 cyclohexane-ethyl acetate mixture yielded 18.7 g of 2-cyano-3-(dimethoxythiophosphoryloxy)-5-methyl-thiophene with a refractive index of $n_D^{20} = 1.539$.

Analysis: $C_8H_{10}NO_3PS_2$. Calculated: %C, 36.50; %H, 3.84; %N, 5.32; %P 11.76. Found: %C, 36.4; %H 4.0; %N, 5.4; %P, 11.4.

EXAMPLE 3

2-cyano-3-diethoxythiophosphoryloxy)-5-methyl-thiophene 7 g of potassium carbonate and 9.5 g of 0,0-diethyl-chlorothiophosphate were added to a solution of 7 g of 2-cyano-3-hydroxy-5-methyl-thiophene in 100 ml of acetone and the mixture was stirred for 15 hours at 20° C. and was then filtered. The filtrate was evaporated to dryness and the residue was chromatographed over silica gel. Elution with an 8-2 cyclohexane-ethyl acetate mixture yielded 11.2 g of 2-cyano-3-(diethoxythiophosphoryloxy)-5-methyl-thiophene with a refractive index of $n_D^{20} = 1.534$.

Analysis: $C_{10}H_{14}NO_3PS_2$. Calculated: %C, 41.23; %H, 4.85; %N, 4.81; %P, 10.63. Found: %C, 41.5; %H, 4.9; %N, 4.7; %P, 10.5.

EXAMPLE 4

2-cyano-3-(dimethoxyphosphoryloxy)-5-methoxy-thiophene

STEP A: methyl 2-ethoxycarbonylimido acetate hydrochloride

Hydrochloric gas was bubbled through a solution of 45.2 g of ethyl cyanacetate in 400 ml of ethyl ether at 20° C. until 20 g had been absorbed and 12.8 g of methanol were added thereto. The mixture was stirred at 20° C. for 8 hours and was then vacuum filtered. The recovered crystals were washed with ether to obtain 39 g of methyl 2-ethoxycarbonylimido acetate hydrochloride melting at 95° to 100° C. The product was used as is for the next step but a dried sample of the product had a melting point of 100°–105° C. (with decomposition).

STEP B: 0-methyl 2-ethoxycarbonyl-thioacetate 250 ml of pyridine at 0° C. were saturated with hydrogen sulfide and after the addition of 39 g of the product of Step A thereto, the hydrogen sulfide was bubbled through the mixture for 2 hours at 0° C. The mixture was then stirred at room temperature for 6 hours and the reaction mixture was poured over ice. The mixture was acidified to a pH of 3 with concentrated hydrochloric acid and was extracted with methylene chloride. The organic extracts were dried and filtered and the filtrate was evaporated to dryness. The residue was rectified to obtain 31 g of 0-methyl 2-ethoxycarbonyl thioacetate with a boiling point of 79° C. at 5 mm Hg.

STEP C: 2-cyano-3-hydroxy-5-methoxy-thiophene 81 g of 0-methyl 2-ethoxycarbonyl-thioacetate and then 38 g of acetonitrile were added to a solution of 27 g of sodium methylate in 250 ml of methanol and the mixture was refluxed for one hour. A solution of 27 g of sodium methylate in 100 ml of methanol were added to the reaction which was cooled to 20° C. and concentrated to dryness. The residue was dissolved in water and the solution was washed with ether, acidified with concentrated hydrochloric acid and was vacuum filtered. The recovered crystals were dried to obtain 42 g of 2-cyano-3-hydroxy-5-methoxy-thiophene with a melting point of 138°–140° C. A microanalytically pure sample obtained by crystallization from isopropyl ether melted at 140° C.

Analysis: $C_6H_5NO_2S$. Calculated: %C, 46.44; %H, 3.25; %N, 9.03; %S, 20.67. Found: %C, 46.5; %H, 3.02; %N, 8,7; %S, 20.5.

STEP D: 2-cyano-3-(dimethoxyphosphoryloxy)-5-methoxy-thiophene 8.4 g of potassium carbonate and 7.1 g of 0,0-dimethyl-chlorophosphate were added to a solution of 9.3 g of 2-cyano-3-hydroxy-5-methoxy-thiophene in 100 ml of acetonitrile and after stirring for 16 hours, the mixture was filtered. The filtrate was evaporated to dryness and the residue was taken up in ether. The ether phase was washed with water and 0.1 sodium hydroxide and dried. The ether phase was evaporated to dryness to obtain 12 g of 2-cyano-3-(dimethoxyphosphoryloxy)-5-methoxy-thiophene with a refraction index of $n_D^{20} = 1.523$.

Analysis: $C_8H_{10}NO_5PS$. Calculated: %C, 36.52; %H, 3.83; %N, 5.32; %P, 11.76. Found: %C, 36.8; %H, 4.0; %N, 5.6; %P 11.5.

EXAMPLE 5

2-cyano-3-(dimethoxyphosphoryloxy)-5-(N-morpholino)-thiophene

STEP A:
2-cyano-3-hydroxy-5-(N-morpholino)-thiophene 40.6 g of methyl N-(morpholinothio-carbonyl)-acetate [Raap, Can. J. Chem., Vol. 46 (1968), p. 2255] were added in small fractions to a mixture of 500 ml of tetrahydrofuran and 10 g of a suspension of 50% of sodium hydride in mineral oil and the mixture was allowed to stand at 20° C. for 2 hours. Then, a solution of 15.5 g of chloroacetonitrile in 500 ml of tetrahydrofuran followed by 500 ml of methanol were added to the reaction mixture which was stirred for 3 hours at 20° C. A solution of 14 g of potassium methylate in 300 ml of methanol was added thereto and the mixture was stirred for 3 hours at 20° C. The mixture was evaporated to dryness and the residue was dissolved in water. The solution was washed with ethyl acetate, was acidified with acetic acid, refrigerated and then vacuum filtered. The recovered crystals were washed with water and dried to obtain 22 g of 2-cyano-3-hydroxy-5-N-morpholino-thiophene melting at 180°–182° C.

Analysis: $C_9H_{10}N_2O_2S$. Calculated: %C, 51.41; %H, 4.80; %N, 13.32; %S, 15.25. Found: %C, 51.1; %H, 4.9; %N, 13.2; %S, 15.2.

STEP B:
2-cyano-3-(dimethoxyphosphoryloxy)-5-(N-morpholino)-thiophene 4.2 g of potassium carbonate and 4.3 g of 0,0-dimethyl chlorophosphate were added to a solution of 6.3 g of 2-cyano-3-hydroxy-5-(N-morpholino)-thiophene in 125 ml of acetonitrile and the mixture was stirred for 8 hours at 20° C. and then was filtered. The filtrate was evaporated to dryness and the residue was dissolved in ethyl acetate. The solution was washed with water and 0.1N sodium hydroxide, dried, treated with activated carbon, filtered and evaporated to dryness. The residue was crystallized from a 10-2 ethyl ether-ethyl acetate mixture to obtain 8 g of 2-cyano-3-(dimethoxyphosphoryloxy)-5-(N-morpholino)-thiophene melting at 80° C.

Analysis: $C_{11}H_{15}N_2O_5PS$. Calculated: %C, 41.51; %H, 4.75; %N, 8.80; %P, 9.73. Found: %C, 41.6; %H, 4.8; %N, 8.8; %P, 9.7.

EXAMPLE 6

2-cyano-3-(dimethoxythiophosphoryloxy)-5-phenyl-thiophene 7 g of potassium carbonate and 8 g of 0,0-dimethyl chlorothiophosphate were added to a solution of 10.5 g of 2-cyano-3-hydroxy-5-phenyl-thiophene in 120 ml of acetone and the mixture was stirred at 20° C. for 15 hours and was then filtered. The filtrate was evaporated to dryness and the crystal residue was empasted with petroleum ether. The crystals were then crystallized from isopropyl ether to obtain 12.8 g of 2-cyano-3-(dimethoxythiophosphoryloxy)-5-phenylthiophene melting at 95° C.

Analysis: $C_{13}H_{12}NO_3PS_2$. Calculated: %C, 48.00; %H, 3.71; %N, 4.31; %P, 9.52. Found: %C, 48.2; %H, 3.9; %N, 4.4; %P, 9.4.

EXAMPLE 7

2,5-dicarbomethoxy-3-(dimethoxythiophosphoryloxy)-thiophene 14 g of potassium carbonate and 16 g of 0,0-dimethyl-chlorothiophosphate were added to a solution of 21.6 g of 2,5-dicarbomethoxy-3-hydroxy-thiophene in 500 ml of acetone and the mixture was stirred for 15 hours at 20° C. and then was filtered. The filtrate was evaporated to dryness and the crystal residue was empasted with petroleum ether, iced and vacuum filtered. The crystals were washed with petroleum ether and were crystallized from methanol to obtain 21 g of 2,5-dicarbomethoxy-3-dimethoxythiophosphoryloxy-thiophene melting at 71° C.

Analysis: $C_{10}H_{13}O_7PS_2$. Calculated: %C, 35.30; %H, 3.85; %P, 9.10. Found: %C, 35.4; %H, 3.9; %P, 9.1.

EXAMPLE 8

2,5-dicarbomethoxy-3-(dimethoxyphosphoryloxy)-thiophene 5.6 g of potassium carbonate and 5.7 g of 0,0-dimethyl-chlorophosphate were added to a solution of 8.6 g of 2,5-dicarbomethoxy-3-hydroxy-thiophene in 100 ml of acetone and the mixture was stirred for 15 hours at 20° C. and was filtered. The filtrate was evaporated to dryness and the residue was dissolved in ethyl ether. The organic solution was washed with 0.1N sodium hydroxide, dried and concentrated to dryness. The residue was crystallized from ethyl ether to obtain 5.2 g of 2,5-dicarbomethoxy-3-(dimethoxyphosphoryloxy)-thiophene melting at 60° C.

Analysis: $C_{10}H_{13}O_8PS$. Calculated: %C, 37.13; %H, 4.03; %P, 9.51. Found: %C, 37.4; %H, 4.1; %P, 9.4.

EXAMPLE 9

2,5-dicarbomethoxy-3-(diethoxythiophosphoryloxy)-thiophene 7 g of potassium carbonate and 8.9 g of 0,0-diethyl chlorothiophosphate were added to a solution of 10.9 g of 2,5-dicarbomethoxy-3-hydroxy-thiophene in 500 ml of acetone and the mixture was stirred for 15 hours at 20° C. and was then filtered. The filtrate was evaporated to dryness and the residue was empasted with a 10-1 petroleum ether-isopropyl ether mixture. The mixture was vacuum filtered and the precipitate was crystallized from ethanol to obtain 8.5 g of 2,5-dicarbomethoxy-3-(diethoxythiophosphoryloxy)-thiophene melting at 50° C.

Analysis: $C_{12}H_{17}O_7PS_2$. Calculated: %C, 39.12; %H, 4.65; %P, 8.41. Found: %C, 39.4; %H, 4.9; %P, 8.4.

EXAMPLE 10

2-carbomethoxy-3-(diethoxythiophosphoryloxy)-5-methyl-thiophene 4.7 g of a 60% suspension of sodium hydride in mineral oil were slowly added to a solution of 20 g of 2-methoxycarbonyl-3-hydroxy-5-methyl-thiophene in 200 ml of dimethylformamide and after stirring the mixture for 1 hour at 20° C., a solution of 22.4 g of O,O-diethylchlorothiophosphate in 50 ml of dimethylformamide was rapidly added thereto. The mixture was stirred for 15 hours at 20° C. and the resulting suspension was poured over a mixture of ice and water. The mixture was extracted with ether and the extracts were dried and concentrated to dryness. The residue was chromatographed over silica gel and elution with a 9-1 cyclohexane-ethyl acetate mixture gave 11.5 g of 2-carbomethoxy-3-(diethoxy-thiophosphoryloxy)-5-methyl-thiophene with a refractive index of $n_D^{22} = 1.5272$.

Analysis: $C_{11}H_{17}O_5PS_2$. Calculated: %C, 40.74; %H, 5.19; %P, 9.55. Found: %C, 40.7, %H, 5.4; %P, 9.0.

EXAMPLE 11

2-benzoyl-3-(dimethoxyphosphoryloxy)-5-methoxy-thiophene 4.2 g of potassium carbonate and 4.3 g of O,O-dimethyl-chlorophosphate were added to a solution of 7.9 g of 2-benzoyl-3-hydroxy-5-methoxy-thiophene in 100 ml of acetonitrile and the mixture was stirred for 16 hours at 20° C. and was filtered. The filtrate was concentrated to dryness and the residue was added to ethyl acetate. The organic solution was washed with water and with 0.1N sodium hydroxide solution saturated with sodium chloride. The mixture was decanted and the organic phase was dried, treated with activated carbon, filtered and evaporated to dryness under reduced pressure. The residue was crystallized from ether and vacuum filtered to obtain 8.2 g of 2-benzoyl-3-(dimethoxyphosphoryloxy)-5-methoxy-thiophene melting at 76° C.

Analysis: $C_{14}H_{15}O_6PS$. Calculated: %C, 49.12; %H, 4.47; %P, 9.05. Found: %C, 49.4; %H, 4.5; %P, 9.0.

EXAMPLE 12

2-carbomethoxy-3-(dimethoxyphosphoryloxy)-5-methoxy-thiophene 7 g of potassium carbonate and 7.2 g of O,O-dimethyl-chlorophosphate were added to a solution of 9.5 g of 2-methoxycarbonyl-3-hydroxy-5-methoxy-thiophene in 125 ml of acetonitrile and the mixture was stirred for 16 hours at 20° C. and was filtered. The filtrate was evaporated to dryness under reduced pressure and the residue was taken up in ethyl acetate. The organic soltuion was washed with water and with an 0.1N sodium hydroxide solution saturated with sodium chloride. The solution was dried and concentrated to dryness. The residue was crystallized from isopropyl ether to obtain 12 g of 2-carbomethoxy-3-(dimethoxyphosphoryloxy)-5-methoxy-thiophene melting at 35° C.

Analysis: $C_9H_{13}O_7PS$. Calculated: %C, 36.49; %H, 4.42; %P, 10.45. Found: %C, 36.7; %H, 4.5; %P, 10.3.

EXAMPLE 13

2-cyano-3-(diethoxythiophosphoryloxy)-5-ethylthio-thiophene

STEP A: 2-cyano-3-hydroxy-5-ethylthio-thiophene 192 g of ethyl α-carbethoxy-dithioacetate [Ber., Vol. 100 (1967), p. 1420] were added at 20° C. to a solution of 70 g of sodium methylate in one liter of methanol and after stirring for 5 minutes at 20° C., 76 g of chloroacetonitrile were added thereto. The mixture was stirred for 1 hour at 45° C. and 2 hours at 20° C. and after the addition of a solution of 70 g of sodium methylate in 500 ml of methanol, the mixture was stirred for 4 hours at 20° C. The mixture was evaporated to dryness under reduced pressure and the residue was dissolved in water. Toluene was added to the aqueous phase which was then acidified by addition of concentrated hydrochloric acid and the organic phase was rapidly separated by decanting. The organic phase was iced and vacuum filtered and the recovered crystals were dried to obtain 97 g of 2-cyano-3-hydroxy-5-ethylthio-thiophene melting at 105° C. A microanalytically pure sample after crystallization from benzene melted at 105° C.

Analysis: $C_7H_7NOS_2$. Calculated: %C, 45.38; %H, 3.81; %N, 7.56; %S, 34.6. Found: %C, 45.6; %H, 4.0; %N, 7.5; %S, 34.4.

STEP B:

2-cyano-3-(diethoxythiophosphoryloxy)-5-ethylthiophene 7 g of potassium carbonate and 9.4 g of O,O-diethyl chlorothiophosphate were added to a solution of 9.3 g of 2-cyano-3-hydroxy-5-ethylthio-thiophene in 150 ml of acetonitrile and the mixture was stirred for 24 hours at 20° C. and was filtered. The filtrate was evaporated to dryness and the residue was chromatographed over silica gel. Elution with an 8-2 cyclohexane-ethyl acetate mixture yielded 14.6 g of 2-cyano-3-(diethoxythiophosphoryloxy)-5-ethylthio-thiophene with a refractive index of $n_D^{20} = 1.5635$.

Analysis: $C_{11}H_{16}NO_3PS_3$. Calculated: %C, 39.16; %H, 4.78; %N, 4.15; %P, 9.18. Found: %C, 39.6; %H, 4.9; %N, 4.0; %P, 9.3.

EXAMPLE 14

2-cyano-3-(diethoxyphosphoryloxy)-5-ethylthio-thiophene 7.7 g of potassium carbonate and 8.6 g of O,O-diethyl-chlorophosphate were added to a solution of 10.1 g of 2-cyano-3-hydroxy-5-ethylthio-thiophene in 150 ml of acetonitrile and the mixture was stirred for 24 hours at 20° C. and was filtered. The filtrate was concentrated to dryness and the residue was dissolved in ether. The ether solution was washed with 0.1N sodium hydroxide solution, dried, treated with activated carbon, filtered and evaporated to dryness to obtain 13 g of 2-cyano-3-(diethoxyphosphoryloxy)-5-ethylthio-thiophene with a refractive index of $n_D^{20} = 1.538$.

Analysis: $C_{11}H_{16}NO_4PS_2$. Calculated: %C, 41.11; %H, 5.02; %N 4.36; %P, 9.64. Found: %C, 40.0; %H, 5.0; %N, 4.2; %P, 9.5.

EXAMPLE 15

2-cyano-3-(dimethoxyphosphoryloxy)-5-ethylthio-thiophene 7.7 g of potassium carbonate and 7.7 g of O,O-dimethyl-chlorophosphate were added to a solution of 10.1 g of 2-cyano-3-hydroxy-5-ethylthio-thiophene in 125 ml of acetonitrile and the mixture was stirred for 8 hours at 20° C. and was filtered. The filtrate was evaporated to dryness and the residue was dissolved in ether. The ether solution was washed with water and 0.1N sodium hydroxide solution, dried, treated with activated carbon, filtered and evaporated to dryness to obtain 12 g of 2-cyano-3-(dimethoxyphosphoryloxy)-5-ethylthio-thiophene with a refractive index of $n_D^{20} = 1.5570$.

Analysis: $C_9H_{12}NO_4PS_2$. Calculated: %C, 36.85; %H, 4.12; %N, 4.77; %P, 10.56. Found: %C, 37.1; %H, 4.1; %N, 4.7; %P, 10.3.

EXAMPLE 16

2-cyano-3-(dimethoxythiophosphoryloxy)-5-ethylthio-thiophene 7 g of potassium carbonate and 8 g of O,O-dimethyl-chlorothiophosphate were added to a solution of 9.3 g of 2-cyano-3-hydroxy-5-ethylthio-thiophene in 125 ml of acetonitrile and the mixture was stirred for 24 hours at 20° C. and was filtered. The filtrate was evaporated to dryness under reduced pressure and the residue was chromatographed over silica gel. Elution with an 8-2 cyclohexane-ethyl acetate mixture yielded 14 g of 2-cyano-3-(dimethoxythiophosphoryloxy)-5-ethylthio-thiophene with a refractive index of $n_D^{20} = 1.5825$.

Analysis: $C_9H_{12}NO_3PS_3$. Calculated: %C, 34.94; %H, 3.91; %N, 4.53; %P, 10.01. Found: %C, 34.9; %H, 3.8; %N, 4.4; %P, 9.8.

EXAMPLE 17

2-cyano-3-(diethoxyphosphoryloxy)-5-methyl-thiophene 11.42 g of potassium carbonate were added to a solution of 11.5 g of 2-cyano-3-hydroxy-5-methyl-thiophene in 80 ml of acetonitrile and after stirring the mixture for 5 minutes, 12.08 g of O,O-diethyl-chlorophosphate were added thereto. The mixture was stirred for 24 hours at room temperature and was filtered. The filtrate was evaporated to dryness and the residue was chromatographed over silica gel. The product was eluted with a 6-4 cyclohexane-ethyl acetate mixture and was dissolved in ethyl acetate. The organic phase was washed with an aqueous sodium hydroxide solution and the organic phase was decanted, and concentrated to dryness to obtain 13 g of 2-cyano-3-(diethoxyphosphoryloxy)-5-methyl-thiophene with a refractive index of $n_D^{21} = 1.502$.

Analysis: $C_{10}H_{14}NO_4PS$. Calculated: %C, 43.63; %H, 5.12; %N, 5.09; %P, 11.25. Found: %C, 43.3; %H, 5.2; %N, 4.9; %P, 11.3.

EXAMPLE 18

2-cyano-3-(dimethoxyphosphoryloxy)-5-n-propyl-thiophene

STEP A: ethyl 3-thioxo-hexanoate 23.7 g of ethyl 3-oxo-hexanoate were added to 100 ml of ethanol saturated with hydrogen chloride gas at −10° C. and then hydrogen sulfide was bubbled therethrough for 6 hours at −10° C. The solvent was evaporated and the residue was dissolved in ether. The solution was washed with water and dried to obtain 25.8 g of ethyl 3-thioxo-hexanoate.

STEP B: 2-cyano-3-hydroxy-5-n-propyl-thiophene

A mixture of 77 g of ethyl 3-thioxo-hexanoate, 300 ml of methanol and 28 g of potassium methylate was stirred at 20° C. for 15 minutes and after the addition of 30.2 g of chloroacetonitrile, thereto, the mixture was stirred for another 15 minutes at 20° C. The mixture was refluxed for 4 hours and the solvent was then evaporated. The residue was dissolved in ether and the ether phase was washed with methylene chloride, acidified with concentrated hydrochloric acid and extracted with ethyl acetate. The solution was then treated with activated carbon, was dried and evaporated to dryness. The residue was dissolved in toluene and the solution was iced and vacuum filtered. The recovered crystals were crystallized from a 3-1 petroleum ether-benzene mixture to obtain 3.1 g of 2-cyano-3-hydroxy-5-n-propyl-thiophene melting at 78° C.

Analysis: $C_8H_9NOS$. Calculated: %C, 57.45; %H, 5.42; %N, 8.37; %S, 19.17. Found: %C, 57.4; %H, 5.3; %N, 8.3; %S, 19.3.

STEP C:
2-cyano-3-(dimethoxyphosphoryloxy)-5-n-propyl-thiophene 2.76 g of potassium carbonate were added to a solution of 3.4 g of 2-cyano-3-hydroxy-5-n-propyl-thiophene in 50 ml of acetonitrile and after stirring the mixture for 5 minutes at 20° C., 2.6 g of O,O-dimethyl-chlorophosphate were added. The mixture was stirred for 20 hours at 20° C. and then filtered. The filtrate was evaporated to dryness and the residue was taken up in ethyl acetate. The solution was washed with 0.01N sodium hydroxide solution, was dried and concentrated to dryness to obtain 5 g of 2-cyano-3-(dimethoxyphosphoryloxy)-5-n-propyl-thiophene with a refractive index of $n_D^{23.5} = 1.507$.

Analysis: $C_{10}H_{14}NO_4PS$. Calculated: %C, 43.63; %H, 5.12; %N, 5.09; %P, 11.25. Found: %C, 43.60; %H, 5.4; %N, 4.9; %P, 10.9.

EXAMPLE 19

2-cyano-3-(ethoxy methylthiophosphonyloxy)-5-methyl-thiophene 14 g of potassium carbonate and 15.9 g of chloro (O-ethylphosphothionate) were added to a solution of 14 g of 2-cyano-3-hydroxy-5-methyl-thiophene in 150 ml of acetonitrile and the mixture was stirred for 24 hours at 20° C. and was then filtered. The filtrate was evaporated to dryness and the residue was chromatographed over silica gel. Elution with an 85-15 cyclohexane-ethyl acetate mixture yielded 19 g of 2-cyano-3-(ethoxymethyl thiophosphonyloxy)-5-methyl-thiophene with a refractive index of $n_D^{20} = 1.5570$.

Analysis: $C_9H_{12}NO_2PS_2$. Calculated: %C, 41.37; %H, 4.63; %N, 5.36; %P, 11.85. Found: %C, 41.3; %H, 4.7; %N, 5.3; %P, 11.6.

EXAMPLE 20

2-cyano-3-(ethoxy-N-isopropylthiophosphoramidoxy)-5-methyl-thiophene 14 g of potassium carbonate and 19 g of O-ethyl N-isopropyl-chlorothiophosphoramidate were added to a solution of 14 g of 2-cyano-3-hydroxy-5-methyl-thiophene in 150 ml of acetonitrile and the mixture was stirred for 24 hours at 20° C. and was then filtered. The filtrate was evaporated to dryness and the residue was chromatographed over silica gel. Elution with an 85-15 benzene-petroleum ether mixture yielded 23 g of 2-cyano-3-(ethoxy-N-isopropylthiophosphoramidoxy)-5-methyl-thiophene with a refractive index of $n_D^{20} = 1.544$.

Analysis: $C_{11}H_{17}N_2O_2PS_2$. Calculated: %C, 43.41; %H, 5.63; %N, 9.20; %P, 10.18. Found: %C, 43.7; %H, 5.8; %N, 8.9; %P, 10.4.

EXAMPLE 21

2-cyano-3-(diethoxythiophosphoryloxy)-5-n-butoxy-thiophene

STEP A: butyl 2-ethoxycarbonylimidoacetate hydrochloride

A hydrogen chloride gas current was bubbled through a solution of 45.2 g of ethyl cyanacetate in 29.6 g of butanol until 16 g were absorbed and the mixture was then stirred for 18 hours at 15° C. The mixture was evaporated to dryness under reduced pressure to obtain 90.5 g of raw butyl 2-ethoxycarbonylimidioacetate hydrochloride which was used as is for the next step.

STEP B: O-n-butyl 2-ethoxycarbonylthioacetate

Hydrogen sulfide was bubbled through 400 ml of pyridine until 30 g were absorbed and then 90.5 g of butyl 2-ethoxycarbonylthioacetate hydrochloride were slowly added thereto at $-15°$ C. The mixture was stirred at 20° C. for 24 hours and was then poured over ice. The mixture was acidified with concentrated hydrochloric acid and extracted with methylene chloride. The organic extracts were dried, filtered and concentrated to dryness. The residue was rectified under reduced pressure to obtain 62.3 g of O-n-butyl 2-ethoxycarbonylthioacetate with a boiling point of 100° C. at 0.4 mm Hg.

STEP C: 2-cyano-3-hydroxy-5-n-butoxy-thiophene 205 g of O-n-butyl 2-ethoxycarbonylthioacetate were added at 30° C. to a solution of 70 g of potassium methylate in a liter of methanol and the mixture was stirred for 10 minutes at 30° C. 75.5 g of chloroacetonitrile were added all at once to the mixture which was stirred for an hour at 40° C. and then a solution of 70 g of potassium methylate in 300 ml of methanol. The mixture was stirred for 6 hours at room temperature and was evaporated to dryness. The residue was washed with ethyl acetate and ether and was dried. The residue was then dissolved in water and the aqueous solution was acidified with concentrated hydrochloric acid and was vacuum filtered. The recovered precipitate was washed with water, dried and chromatographed over silica gel. Elution with 6-4 cyclohexane-ethyl acetate yielded 81 g of 2-cyano-3-hydroxy-5-n-butoxy-thiophene melting at 107° C.

Analysis: $C_9H_{11}NO_2S$. Calculated: %C, 54.80; %H, 5.62; %N, 7.10; %S, 16.25. Found: %C, 55.1; %H, 5.7; %N, 7.0; %S, 16.3.

STEP D:
2-cyano-3-(diethoxythiophosphoryloxy)-5-n-butoxy-thiophene 7 g of potassium carbonate and 9.4 g of O,O-diethyl chlorothiophosphate were added to a solution of 9.8 g of 2-cyano-3-hydroxy-5-n-butoxy-thiophene in 150 ml of acetonitrile and the mixture was stirred for 24 hours at 20° C. and was filtered. The filtrate was evaporated to dryness under reduced pressure and the residue was chromatographed over silica gel. Elution with benzene yielded 14 g of 2-cyano-3-(diethoxythiophosphoryloxy)-5-n-butoxy-thiophene with a refractive index of $n_D^{20}$ = 1.525.

Analysis: $C_{13}H_{20}NO_4PS_2$. Calculated: %C, 44.69; %H, 5.77; %N, 4.01; %P, 8.85. Found: %C, 44.8; %H, 5.9; %N, 3.9; %P, 8.9.

EXAMPLE 22

2-cyano-3-(dimethoxythiophosphoryloxy)-5-n-butoxy-thiophene 7 g of potassium carbonate and 8 g of O,O-dimethyl chlorothiophosphate were added to a solution of 9.8 g of 2-cyano-3-hydroxy-5-n-butoxy-thiophene in 150 ml of acetonitrile and the mixture was stirred for 24 hours at 20° C. and was then filtered. The filtrate was evaporated to dryness and the residue was chromatographed over silica gel. Elution with benzene yielded 11 g of 2-cyano-3-(dimethoxythiophosphoryloxy)-5-n-butoxy-thiophene with a refractive index of $n_D^{20}$ = 1.5375.

Analysis: $C_{11}H_{16}NO_4PS_2$. Calculated: %C, 41.11; %H, 5.02; %N, 4.37; %P, 9.64. Found: %C, 41.1; %H, 5.0; %N, 4.3; %P, 9.5.

EXAMPLE 23

2-cyano-3-(diethoxyphosphoryloxy)-5-n-butoxy-thiophene 7.7 g of potassium carbonate and 8.6 g of O,O-diethyl chlorophosphate were added to a solution of 11 g of 2-cyano-3-hydroxy-5-n-butoxy-thiophene in 150 ml of acetonitrile and the mixture was stirred for 16 hours at room temperature and was then filtered. The filtrate was evaporated to dryness and the residue was taken up in ethyl ether. The ether phase was washed with an aqueous solution of 100 g/l of sodium chloride and then with an aqueous 0.1N sodium hydroxide solution containing 100 g/l of sodium chloride. The solution was dried, treated with activated carbon, filtered and evaporated to dryness under reduced pressure to obtain 15.5 g of 2-cyano-3-(diethoxyphosphoryloxy)-5-n-butoxy-thiophene with a refractive index of $n_D^{20}$ = 1.500.

Analysis: $C_{13}H_{20}NO_5PS$. Calculated: %C, 46.85; %H, 6.05; %N, 4.2; %P, 9.29. Found: %C, 47.0; %H, 6.1; %N, 4.1; %P, 9.0.

EXAMPLE 24

2-cyano-3-(dimethoxyphosphoryloxy)-5-n-butoxy-thiophene 7.7 g of potassium carbonate and 7.7 g of O,O-dimethyl chlorophosphate were added to a solution of 11 g of 2-cyano-3-hydroxy-5-n-butoxy-thiophene in 150 ml of acetonitrile and the mixture was stirred for 16 hours at 20° C. and was filtered. The filtrate was evaporated to dryness under reduced pressure and the residue was dissolved in ether. The ether solution was washed with water containing 100 g/l of sodium chloride and then with 0.1N sodium hydroxide solution containing 100 g/l of sodium chloride. The ether phase was dried and treated with activated carbon, filtered and concentrated to dryness to obtain 12.5 g of 2-cyano-3-(dimethoxyphosphoryloxy)-5-n-butoxy-thiophene with a refractive index of $n_D^{20}$ = 1.511.

Analysis: $C_{11}H_{16}NO_5PS$; molecular weight = 305.29. Calculated: %C, 43.28; %H, 5.28; %N, 4.59; %P, 10.15. Found: %C, 43.7; %H, 5.4; %N, 4.6; %P, 9.6.

EXAMPLE 25

An emulsifiable insecticide concentrate was prepared containing 15% by weight of 2-cyano-3-(dimethoxyphosphoryloxy)-5-methyl-thiophene (compound A), 6.4% by weight of Atlox 4851 (oxyethylene triglyceride with a sulfonate- an acid No. of 1.5), 3.2% by weight of Atlox 4855 (oxyethylene triglyceride with a sulfonate-acid No. 3) and 75.4% by weight of xylene.

EXAMPLE 26

An emulsifiable acaricide concentrate was prepared containing 25% by weight of 2-cyano-3-(dimethoxyphosphoryloxy)-5-methyl-thiophene (compound A), 6.4% by weight of Atlox 4851, 3.2% by weight of Atlox 4855 and 65.4% by weight of xylene.

EXAMPLE 27

An emulsifiable nematocide concentrate used to treat soil was prepared containing 45% by weight of 2-cyano-3-(dimethoxyphosphoryloxy)-5-methyl-thiophene (compound A), 6.4% by weight of Atlox 4851, 3.2% by weight of Atlox 4855 and 45.4% by weight of xylene.

Insecticidal activity of the 2-cyano-3-(dimethoxyphosphoryloxy)-5-methyl-thiophene (compound A) and the 2-cyano-3-(dimethoxyphosphoryloxy)-5-methoxy-thiophene (compound B).

A. Drosophila melanogaster

This test measured the activity of the vapors of 2-cyano-3-(dimethoxyphosphoryloxy)-5-methyl-thiophene (compound A) and 2-cyano-3-(dimethoxyphosphoryloxy)-5-methoxythiophene (compound B). The insects were placed in a Petri dish with a diameter of 10 cm connected with a tergal gauze to a crystallizer of the same diameter into which was placed an acetone solution of the test compound which was evaporated before introduction of the insects. Three tests were run for each concentration using 25 adult insects less than 48 hours old and the results were expressed as percent of mortality after 1 hour and 4 and 6 hours. The results are reported in Table I.

TABLE I

| Compound | Concentration in ppm/Time in hrs. | 500 | 50 | 5 |
| --- | --- | --- | --- | --- |
| A | 1 | 100 | 100 | 40 |
|   | 4 | 100 | 100 | 100 |
|   | 6 | 100 | 100 | 100 |
| B | 1 | 40 | 29 | 0 |
|   | 4 | 100 | 100 | 82 |
|   | 6 | 100 | 100 | 96 |

B. Blattella germanica

This was a topical application test in which adult males of Blattella germanica received 2 microliters of an acetone solution of the test compound between the second and third pair of feet. After treatment, the test insects were held in dim light at 20° C. and were fed and the percent of mortality was determined at 24 and 48 hours and 6 days with the results being reported in Table II.

TABLE II

| Compound | Concentration in ppm/time | 5000 | 1250 | 62.5 |
| --- | --- | --- | --- | --- |
| A | 24 hrs. | — | 45 | 5 |
|   | 48 hrs. | — | 65 | 10 |
|   | 6 days | — | 100 | 30 |
| B | 24 hrs. | 100 | 95 | 0 |
|   | 48 hrs. | 100 | 95 | 15 |
|   | 6 days | 100 | 95 | 35 |

C. Sitophilus granarius

This test was effected by topical application of the test compounds in acetone solution at a rate of 5000 or 500 mg of active compound per liter. 0.2 μl of the acetone solution was applied to the ventral thorax of Sitophilus Granarius of 50 insects per concentration and per test. The number of insects living and dead was determined after 4 and 24 hours and 5 days. The results are reported in Table III.

TABLE III

| Compound | Concentration in ppm/time | 5000 | 500 |
| --- | --- | --- | --- |
| A | 4 hrs | 100 | 90 |
|   | 24 hrs | 100 | 90 |
|   | 5 days | 100 | 100 |
| B | 4 hrs | 100 | 49 |
|   | 24 hrs | 100 | 100 |
|   | 5 days | 100 | 100 |

D. Musca domestica

This topical application test comprised applying a microliter of an acetone solution of the test product to the dorsal thorax of flies which has been put to sleep with ether. The insects were held at 20° C. and 50% relative humidity. The insects were fed milk and water and the percent of mortality was determined after one hour and 24 hours after treatment. The results were reported in Table IV.

TABLE IV

| Compound | Concentration in ppm/Time | 2500 | 500 | 100 | 50 |
| --- | --- | --- | --- | --- | --- |
| A | 1 | — | 100 | 100 | 95 |
|   | 24 | — | 100 | 100 | 95 |
| B | 1 | 100 | 100 | 87 | 79 |
|   | 24 | 100 | 100 | 94 | 92 |

E. Alphis fabae

This test was effected in the open air with plots of beans measuring 360 × 120 cm with 4 rows of beans. When natural contamination with Aphis fabae was estimated to be sufficient, each plot was sprayed with an aqueous solution of compound A with two plots being used for each dose. The treatment was effected with a base of 2 liters of spray solution. The controls of the population was effected 1 hour before the treatment then 1 day, 1,2 and 3 weeks after the treatment.

The readings were made on the following scale with 20 plots being read for each of the doses. The results are in Table V (compound A at 50 g/hl).

The notation was effected per class:
0 corresponding at 0 aphis living per colony
1 corresponding at 1 to 30 living aphids per colony
2 corresponding at 30 to 50 living aphids per colony
3 corresponding at 150 to 500 living aphids per colony
4 corresponding at 500 living aphids per colony

TABLE V

|  | Compound A | | Controls | |
| --- | --- | --- | --- | --- |
|  | Average value | No. of aphids | Average value | No. of aphids |
| 1 hour before test | 1.47 | 84.8 | 1.53 | 101.8 |
| 1 day after test | 0 | 0 | 1.89 | 131.3 |
| 1 week after test | 0.14 | 1.3 | 2.93 | 314.3 |
| 2 weeks after test | 0.84 | 13.6 | 3.32 | 314.5 |
| 3 weeks after test | 2.28 | 140.9 | 2.26 | 197.0 |

F. Systemic activity in bean stalk against *Aphis fabae*

Vicia fabae stalks about 30 cm high were wrapped in hydrophilic cotton for a length of about 5 cm and the cotton was itself enclosed in a plastic envelope so as to avoid an eventual effect of the product by its vapors. A value of 2 ml of an aqueous solution of compound A at a concentration of 0.1 and 1 g/liter was injected into the dressing with a syringe and 3 bean plants were used for each concentration. Each plant was then contaminated with about 20–25 apterous individual adult Aphis fabae and the number of dead insects was noted 1 and 2 days after contamination and their eventual decendents after one week. The dead insects necessarily resulted from the translation of the product from the stalk to the leaves and the results are reported in Table VI.

TABLE VI

| Dose of A in g/l | % Efficacy after 24 hr. | 48 hr. | Observations of Decendents after 1 week |
|---|---|---|---|
| 1 | 88.6 | 100 | No decendents |
| 0.1 | 41.4 | 48.7 | " |

The foregoing tests show that compounds A and B have an interesting insecticidal activity against the species tested. The systemic activity of compound A in bean plants against Aphis fabae is particularly noteworthy as systemic insecticides constitute a special useful class of insecticides.

Acaricide activity of the 2-cyano-3-(dimethoxyphosphoryloxy)-5-methyl-thiophene (compound A) on Tetranychus urticae.

A. Ovicide test

Bean leaves infested with 10 females of *Tetranychus urticae* per leaf were used and glue was placed about the edge thereof. The females were left for 24 hours and then removed and the leaves infested with eggs were divided into 2 groups. The first group was treated by spraying each leaf with 0.5 ml of an aqueous solution of compound A at concentration of 50 and 100 mg per liter and the second group was untreated and acted as controls. The number of eggs living after 9 days from the beginning of treatment and the percent of mortality of eggs was determined in Table VII.

TABLE VII

| Product | Concentration in mg/l | % mortality |
|---|---|---|
| A | 50 | 54.3 |
|   | 10 | 45.4 |
| Controls | 0 | 9.9 |

B. Adulticide test

Bean leaves with glue about the edges and infested with 25 Tetranychus urticae acariens each were divided into 2 groups. The first group of leaves were sprayed with 2.5 ml each of an aqueous solution of 50, 10 and 1 mg/l of compound A. The second group were untreated and acted as controls. The number of acariens living after 48 hours after the spraying and the results are reported in Table VIII.

TABLE VIII

| Compound | Concentration in mg/l | % mortality |
|---|---|---|
| A | 50 | 94.0 |
|   | 10 | 54.6 |
| Controls | 0 | 5.0 |

C. Larvicide test

The procedure was the same as the ovicide test but the readings were taken 9 days after treatment to determine the insects evolved in that time. The results are expressed in Table IX.

TABLE IX

| Compound | Concentration in mg/l | % mortality |
|---|---|---|
| A | 50 | 100 |
|   | 10 | 86.6 |
| Controls | 0 | 12.5 |

These three tests demonstrate that compound A has a good acaricide activity against *Tetranychus urticae*.

Nematocide activity of the 2-cyano-(3-dimethoxyphosphoryloxy-5-methyl-thiophene (compound A).

A. Panagrellus silusae

About 2000 nematodes of Panagrellus silusae suspended in 0.5 ml of water were placed in a container of about 50 ml and then 10 ml of an aqueous solution of compound A in concentrations of 1 or 0.1 g/l were added. Three tests were run for each concentration and after 24 hours, the aqueous media was homogenized. The number of nematodes living and dead in one ml of solution, with a Peter slide, were determined. The results are expressed as % of mortality as compared to the untreated controls and the results were 94.7% at a dose of 0.1 g/l and 21.4% at a dose of 0.01 g/l. This means that compound A shows an interesting nematocidal activity.

Various modifications of the products and method of the invention may be made without departing from the spirit or scope thereof and it is to be understood that the invention is to be limited only as defined in the appended claims.

We claim:

1. A compound of the formula

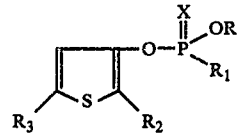

wherein R is alkyl of 1 to 4 carbon atoms, $R_1$ is alkoxy of 1 to 4 carbon atoms, $R_2$ is cyano, $R_3$ is selected from the group consisting of alkyl of 1 to 6 carbon atoms, alkoxy of 1 to 6 carbon atoms and alkylthio of 1 to 6 carbon atoms and phenyl and X is selected from the group consisting of oxygen and sulfur.

2. A compound of claim 1 wherein R is alkyl of 1 to 4 carbon atoms, R is alkoxy of 1 to 4 carbon atoms, X is oxygen, $R_2$ is cyano and $R_3$ is selected from the group consisting of alkyl of 1 to 6 carbon atoms and alkoxy of 1 to 6 carbon atoms.

3. A compound of claim 1 which is 2-cyano-3-(dimethoxyphosphoryloxy)-5-methyl-thiophene.

4. A compound of claim 1 which is 2-cyano-3-(dimethoxyphosphoryloxy)-5-methoxy-thiophene.

5. A compound of claim 1 which is 2-cyano-3-(dimethoxyphosphoryloxy)-5-ethylthio-thiophene.

6. A compound of claim 1 which is 2-cyano-3-(dimethoxythiophosphoryloxy)-5-methyl-thiophene.

7. A compound of claim 1 which is 2-cyano-3-diethoxythiophosphoryloxy)-5-methyl-thiophene.

8. A compound of claim 1 which is 2-cyano-3-(dimethoxythiophosphonyloxy)-5-ethylthio-thiophene.

* * * * *

UNITED STATES PATENT OFFICE
CERTIFICATE OF CORRECTION

Patent No. 4,128,562                    Dated  Dec. 5, 1978

Inventor(s) JACQUES PERRONNET and LAURENT TALIANI

It is certified that error appears in the above-identified patent and that said Letters Patent are hereby corrected as shown below:

| Col. | Line Claim 2 | Page | Line | | |
|---|---|---|---|---|---|
| 16 | 53 | 36 | 2 | "R" should be | $--R_1--$ |

Signed and Sealed this

Nineteenth Day of June 1979

[SEAL]

Attest:

RUTH C. MASON
*Attesting Officer*

DONALD W. BANNER
*Commissioner of Patents and Trademarks*